United States Patent
Busch et al.

(10) Patent No.: US 6,770,783 B1
(45) Date of Patent: Aug. 3, 2004

(54) METHOD FOR PRODUCING ACID CHLORIDES

(75) Inventors: Ralph Busch, Worms (DE); Heinz-Josef Kneuper, Niederkirchen (DE); Theodor Weber, Ludwigshafen (DE); Winfried Müller, Mannheim (DE); Armin Stamm, Mainz (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 107 days.

(21) Appl. No.: 10/070,864
(22) PCT Filed: Aug. 31, 2000
(86) PCT No.: PCT/EP00/08515
  § 371 (c)(1),
  (2), (4) Date: Mar. 12, 2002
(87) PCT Pub. No.: WO01/19768
  PCT Pub. Date: Mar. 22, 2001

(30) Foreign Application Priority Data

Sep. 13, 1999  (DE) ......................................... 199 43 844

(51) Int. Cl.⁷ .............................................. C07C 51/58
(52) U.S. Cl. ..................................................... 562/857
(58) Field of Search ......................................... 562/857

(56) References Cited

U.S. PATENT DOCUMENTS 4,900,479 A  2/1990  Freudenberg et al.
5,166,427 A  11/1992 Hohmann et al.
5,200,560 A  4/1993  Kahl et al.
5,245,063 A  9/1993  Ksoll et al.
5,430,186 A  7/1995  Ksoll et al.

FOREIGN PATENT DOCUMENTS

DE  0 153 867    2/1982
DE  0 43 37 785  5/1995
EP  0 296 404   12/1988
EP  0 367 050    5/1990
EP  0 452 806   10/1991
EP  0 475 137    3/1992
EP  0 635 473    1/1995

OTHER PUBLICATIONS

Pizey "Synthic Reagents" vol. 1, Chapter 4 (1974) pp. 321–357.
Patai "The chemistry of acyl halides" Chapter 2 (1972) pp. 35–68.
Bosshard et al. "176. Eine Methode zur katalysierten Herstellung von Carbonsäure–und Sulfosäuer–chloriden mit Thionylchlorid[1]" Helvetica Chimica Acta Volumen XLII, Fasciculus V (1959) No. 175–176 pp. 1653–1658.

Primary Examiner—Paul J. Killos
(74) Attorney, Agent, or Firm—Keil & Weinkauf

(57) ABSTRACT

The invention relates to a method for producing acid chlorides by converting carboxylic acids with carbon oxychlorides or thionyl chloride in the presence of a catalyst adduct of an N,N-disubstituted formamide of general formula (I) and carbon oxychloride or thionyl chloride. In the formula, $R^1$ and $R^2$, independently from one another, mean $C_1$- to $C_4$-alkyl or $R^1$ and $R^2$ together mean a $C_4$- or $C_5$-alkylene chain. According to the inventive method, hydrogen chloride is added during and/or after the conversion.

12 Claims, No Drawings

METHOD FOR PRODUCING ACID CHLORIDES

The present invention relates to a process for the preparation of carbonyl chlorides by reacting the corresponding carboxylic acids with phosgene or thionyl chloride in the presence of a catalyst adduct with the simultaneous and/or subsequent introduction of hydrogen chloride, which leads to carbonyl chlorides which have a low color number.

Carbonyl chlorides are important intermediates in the synthesis of a large number of chemical products, in particular pharmaceuticals, cosmetics, surfactants and paper auxiliaries. They can be prepared by reacting carboxylic acids with chlorinating agents, such as $PCl_3$, $POCl_3$, $SOCl_2$, $SO_2Cl_2$ or $COCl_2$. Of industrial importance are, in particular, the reactions with thionyl chloride, phosphorus trichloride and phosgene.

As a rule, in the synthesis via phosphorus trichloride, one reactant (carboxylic acid or phosphorus trichloride) is initially introduced, and the other reactant (phosphorus trichloride or carboxylic acid) is slowly added. Where appropriate, the synthesis is carried out in a solution diluted with a reaction-inert solvent (e.g. toluene). After removal of the phosphorous acid formed, the carbonyl chloride is as a rule purified by distillation. The addition of a catalyst is not required.

EP-A-0 296 404 describes the purification of crude carbonyl chlorides which originate from the chlorination using phosphorus trichloride, in which the reaction products are treated with carboxamide hydrohalides. The crude carbonyl chloride solutions from the phosphorus trichloride route differ in composition from those obtainable by the phosgene or thionyl chloride route. For example, the latter have:

(i) a considerably higher content of undesired minor components.

(ii) a varying composition of the minor components, which is influenced by the choice of chlorinating agent.

(iii) supplementary to the varying composition of the minor components, also the presence of degradation and/or secondary products from the catalyst adducts used.

The use of phosgene or thionyl chloride instead of phosphorus trichloride generally leads to a higher conversion and better selectivity. Both chlorinating agents additionally have the advantage over phosphorus trichloride that only gaseous byproducts are formed, which either escape in the form of gas during the synthesis or can be completely expelled by stripping with an inert gas when the reaction is complete. Furthermore, phosgene, in particular, is a very good value chlorinating agent.

Thionyl chloride and, in particular, phosgene are less reactive as chlorinating agents compared with phosphorus trichloride. The preparation of carbonyl chlorides by reacting carboxylic acids with thionyl chloride is therefore preferably carried out in the presence of a catalyst to increase the reaction rate. In the preparation by reaction with phosgene, a catalyst is always used. Catalyst precursors which are suitable for both chlorinating agents are N,N-disubstituted formamides and hydrochlorides thereof, and also pyridine or urea. Overviews relating to the chlorination by means of thionyl chloride are given in M. F. Ansell in S. Patai, "The Chemistry of Acyl Halides", John Wiley and Sons, New York 1972, 35–69 and H. H. Bosshard et al., Helv. Chem. Acta 62 (1959) 1653–1658 and S. S. Pizey, Synthetic Reagents, Vol. 1, John Wiley and Sons, New York 1974, ISBN 853120056, 321–557, in particular 333–335. Both by the phosgene route and also by the thionyl chloride route preference is given to using N,N-disubstituted formamides. These react with said chlorinating agents to give the Vilsmeier salts.

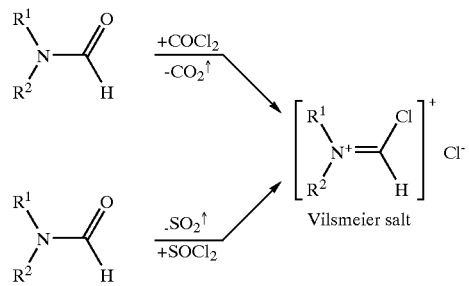

The Vilsmeier salt, the actual reactive chlorinating reagent, reacts with the carboxylic acid or the carboxylic anhydride to give the acid chloride. In the process, formamide-hydrochloride is reformed, which can in turn react with phosgene or thionyl chloride to give the Vilsmeier salt and passes through further catalyst circuits. The N,N-disubstituted formamide-hydrochlorides or vilsmeier salts thereof are not, however, very thermally stable, meaning that it is possible for secondary reactions to take place above 80 to 90° C.

The preferred use of N,N-disubstituted formamides as catalyst precursor for the phosgenation of carboxylic acids also emerges from EP-A-0 367 050, EP-A-0 452 806, DE-A-4 337 785, EP-A-0 475 137 and EP-A-0 635 473.

As regards the color number, in the chlorination of carboxylic acids using phosgene or thionyl chloride, the use of catalysts has an adverse effect. Although these catalysts are separated off by phase separation following the chlorination, they can, however, remain in the product in small amounts and lead either themselves or as degradation or secondary products to yellow colorations of the carbonyl chlorides. For this reason, the carbonyl chlorides prepared via phosgene or thionyl chloride are generally purified by distillation to give largely colorless products. Such a distillation is not only an energy- and time-consuming operation, but also harbors a number of further disadvantages. Many longer-chain carbonyl chlorides cannot be distilled without partial decomposition. Furthermore, it is known that the distilled products can become contaminated as a result of decomposition of the catalyst still present in the distillation bottoms. Relatively large amounts of accumulated catalyst residue also represent a safety risk during the distillation since at elevated temperature there is the risk of spontaneous decomposition.

A further method of purifying the crude carbonyl chlorides is the treatment with activated carbons. However, these absorptive purification steps are industrially complex and, moreover, are not always successful. In addition, a contaminated solid forms, which has to be subsequently disposed of in the correct manner.

It is an object of the invention to develop a process for the preparation of carbonyl chlorides by reacting the corresponding carboxylic acids with phosgene or thionyl chloride which no longer has the known disadvantages and leads to carbonyl chlorides which have a low color number.

We have found that this object is achieved by the development of a process for the preparation of carbonyl chlorides by reacting carboxylic acids with phosgene or thionyl chloride in the presence of a catalyst adduct of an N,N-disubstituted formamide of the formula (I)

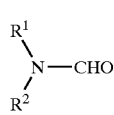

in which R¹ and R² independently of one another are $C_1$- to $C_4$-alkyl, or R¹ and R² together are a $C_4$- or $C_5$-alkylene chain, and phosgene or thionyl chloride, which comprises introducing hydrogen chloride during and/or after the reaction.

By the process according to the invention, it is possible to prepare carbonyl chlorides by reacting the corresponding carboxylic acids with phosgene or thionyl chloride in high yield and with low color number. A low color number here means a color number which is at most 50% of the APHA color number, or in the case of unsaturated carbonyl chlorides, at most 75% of the iodine color number which is achieved using the process of the prior art, i.e. without the inventive measure. The determinations of the APHA color number and of the iodine color number are described in the standard DIN EN 1557 (March 1997).

The inventive introduction of the hydrogen chloride can be carried out in a variety of ways. For example, the hydrogen chloride can be introduced, with regard to the introduction of the chlorinating agent phosgene or thionyl chloride, exclusively during its addition, during and after its addition or exclusively after its addition. Preference is given to metering in the hydrogen chloride at the same time as the chlorinating agent is added. In the three variants mentioned, the hydrogen chloride can be introduced continuously, i.e. without interruption, or with one or more interruptions, to a pulse-like metered addition. In addition, the rate of addition of the hydrogen chloride within an addition interval can remain constant or can decrease or increase. Within the meaning of a constant working of the reaction, it is advantageous to introduce the hydrogen chloride continuously, where an interruption, for example in the sense of a subsequent increase in the hydrogen chloride concentration, can still be entirely advantageous.

For the process according to the invention, it is immaterial whether the hydrogen chloride is added at one site together with the chlorinating agent or at another site, spatially separate from the chlorinating agent. What is essential, however, is that the reaction solution is thoroughly mixed during the reaction with the chlorinating agent, and also during the introduction of the hydrogen chloride, and the presence of the catalyst phase during the introduction of hydrogen chloride. The catalyst phase is advantageously separated off only after all of the hydrogen chloride has been added.

In the preparation of the carbonyl chlorides according to the invention, the catalyst used is a catalyst adduct formed from the reaction of phosgene or thionyl chloride with an N,N-disubstituted formamide. The latter, which is also referred to as a catalyst precursor, is defined by the formula (I)

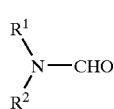

in which R¹ and R² independently of one another are a $C_1$- to $C_4$-alkyl, specifically methyl, ethyl, propyl, 1-methylethyl, butyl, 1-methylpropyl, 2-methylpropyl and 1,1-dimethylethyl, or together are a $C_4$- or $C_5$-alkylene chain, specifically $CH_2CH_2CH_2CH_2$ or $CH_2CH_2CH_2CH_2CH_2$.

It is important that the mutual solubility of the carbonyl chlorides and of the hydrochlorides of the N,N-disubstituted formamides (I) formed by the introduction of hydrogen chloride is low and that two isolatable phases form.

Preference is given to using N,N-dimethylformamide.

The formation of the catalyst adduct can either be carried out in the apparatus where the chlorination is carried out, or else upstream in another apparatus. In the last-mentioned case, a certain amount of the N,N-disubstituted formamide is introduced into a separate apparatus and saturated with hydrogen chloride, and the desired amount of phosgene or thionyl chloride is introduced. The mixture can then be transferred to the actual reaction apparatus. In the first-mentioned case, the procedure described is carried out directly in the reaction apparatus. Preference is given to bringing the carboxylic acid into contact with the N,N-disubstituted formamide (I) and subsequently simultaneously introducing the chlorinating agent and the hydrogen chloride. If the process is operated with catalyst recycle, the carboxylic acid is brought into contact with the recycled catalyst and optionally fresh N,N-disubstituted formamide (I), and then the chlorinating agent and hydrogen chloride are introduced as described above.

The amount of N,N-disubstituted formamide (I) to be used is dependent on the type of chlorinating agent. If phosgene is used, a molar amount of N,N-disubstituted formamide (I) of from 0.05 to 2.0 is advantageously used, preferably from 0.1 to 1.0 and particularly preferably from 0.1 to 0.6, based on the molar amount of carboxylic acid used. If thionyl chloride is used, the corresponding advantageous range is between 0.001 and 0.05 and preferably between 0.001 and 0.01.

The reaction between the carboxylic acid and phosgene or thionyl chloride is generally carried out at temperatures from 0 to 100° C., preferably from 20 to 80° C., particularly preferably from 20 to 60° C. The reaction is generally carried out at a pressure of from 0.5 to 2.0 bar abs, preferably from 0.8 to 1.2 bar abs, particularly preferably at atmospheric pressure. Suitable reaction apparatuses which may be mentioned are the apparatuses known to the person skilled in the art for reactions in the liquid/liquid and gas/liquid phase, such as, for example, stirred-tank reactors or batteries of stirred-tank reactors with appropriate gas inlet and gas distribution technology.

The molar amount of phosgene or thionyl chloride added overall during the reaction to give the carbonyl chloride is from 1.0 to 2.0, based on the molar amount of the carboxylic acid used. Preference is given to a molar amount of from 1.0 to 1.3, based on the molar amount of the carboxylic acid used.

The molar amount of hydrogen chloride to be introduced overall during the process according to the invention is dependent on the molar amount of carboxylic acid used and is advantageously in the range between 0.2 and 2.0, based on the molar amount of carboxylic acid used. Preference is given to a molar amount of from 0.5 to 1.5, based on the molar amount of carboxylic acid used. As already explained above, in the process according to the invention, hydrogen chloride can be introduced during and/or after the reaction of the carboxylic acids with phosgene or thionyl chloride. The specified molar amount of hydrogen chloride corresponds to the cumulative molar amount over the entire process. In the case of a continuous procedure, the relative molar amounts given are to refer to the time unit where, in this case, both the molar amount of the freshly introduced N,N-disubstituted formamide (I) and also that of the recycled catalyst are to be used.

Following the reaction with the chlorinating agent, the reaction mixture can be thoroughly mixed for a further period, where, depending on the embodiment, further hydrogen chloride can also be introduced. The subsequent, thorough mixing is generally carried out for one hour at most, but, depending on the reaction system and desired product purity, can also be dispensed with. In addition, it is also possible, after addition of the chlorinating agent is complete, to add yet further N,N-disubstituted formamide, preferably with the further introduction of hydrogen chloride or as a hydrochloride, and mix thoroughly. This can, for example, be added following the chlorination using thionyl chloride in order to increase the amount of extractant.

An essential feature for achieving a low color number of the carbonyl chlorides prepared is the composition of the catalyst-containing phase following the reaction. The lower the content of catalyst adduct, the lower, too, the achievable color number of the carbonyl chlorides. The molar content of the catalyst adduct, based on the total molar amount of N,N-disubstituted formamide (I) plus catalyst adduct, is advantageously less than 0.3 according to the process according to the invention. Preference is given to a relative content of less than 0.1, particularly preferably of less than 0.05. The relative content can be adjusted via the added amount of chlorinating agent and of hydrogen chloride.

The carbonyl chlorides and the catalyst-containing phase are advantageously isolated by phase separation. This can be carried out either in the reaction apparatus used above, provided it is suitable for this purpose, or else in a separate apparatus. Suitable apparatuses are, for example, stirred-tank reactors, batteries of stirred-tank reactors or phase-separating vessels, such as "mixer settlers". In general, both phases have separated within 2 hours. For isolation, it is also possible to use suitable filters, such as, for example, coalescence filters of known construction.

The carbonyl chlorides prepared in this way have a considerably lower color number than carbonyl chlorides prepared in accordance with the prior art without the measure according to the invention, and can then as a rule be used directly for further synthesis stages. If required, they can, however, also be subjected to still further treatment procedures. Examples which may be mentioned are the treatment with a hydrochloride of an N,N-disubstituted formamide, distillation or adsorptive purification.

According to an advantageous embodiment of the process, the separated-off catalyst-containing phase, comprising N,N-disubstituted formamide (I) and catalyst adduct, can be reused as catalyst precursor in the further synthesis. For this, the catalyst-containing phase is returned to the synthesis stage, as already described. It is advantageous to bleed some of the catalyst-containing phase from the system in order to avoid a buildup of undesired secondary components.

The process according to the invention can either be carried out batchwise or continuously.

(a) batchwise preparation:

In the batchwise preparation, the reaction mixture, consisting of the carboxylic acid and the N,N-disubstituted formamide (I) or the catalyst adduct, prepared from phosgene or thionyl chloride and the N,N-disubstituted formamide (I), is introduced into a reaction apparatus, for example a stirred-tank reactor. Then, the desired amount of liquid or gaseous phosgene or thionyl chloride, and, in parallel thereto, the desired amount of hydrogen chloride is added over a certain period of time. The time requirement for the addition of the chlorinating agent depends on the reaction rate and can generally be limited to a few hours. Depending on the embodiment, in one variant, the introduction of hydrogen chloride ends with the completion of the addition of the chlorinating agent or, in another variant, is maintained beyond that. When the addition of hydrogen chloride is complete, the reaction solution is generally left to stand for 1 to 2 hours, and the two phases are separated from one another. As a rule, the carbonyl-chloride-containing phase is the upper one, and the catalyst-containing phase is the lower one.

It may be expressly pointed out that, in a third variant, the introduction of hydrogen chloride according to the invention can also be started only after the introduction of the chlorinating agent is complete. In this case, the reaction with the chlorinating agent would take place without the introduction of hydrogen chloride.

(b) continuous preparation:

Reaction apparatuses suitable for the continuous procedure are, for example, stirred-tank reactors, batteries of stirred-tank reactors or reaction columns operated countercurrently. If a stirred-tank reactor is used, the carboxylic acid and the N,N-disubstituted formamide (I) or the catalyst adduct, prepared from phosgene or thionyl chloride and the N,N-disubstituted formamide (I), are introduced, and liquid or gaseous phosgene or thionyl chloride and, in parallel thereto, the desired amount of hydrogen chloride are added. After an amount of chlorinating agent which is approximately equivalent to the carboxylic acid has been introduced, the simultaneous introduction of carboxylic acid and N,N-disubstituted formamide (I) and catalyst adduct, and an amount of phosgene or thionyl chloride which is essentially equimolar to the added carboxylic acid, is started. In addition, the desired amount of hydrogen chloride is introduced continuously. An amount of the reaction volume corresponding to the reactants introduced is removed from the reaction apparatus, for example by maintaining the level, and passed to a separating vessel. In the separating vessel, the carbonyl chloride can be continuously removed as the upper phase, and the catalyst-containing, lower phase can be continuously returned to the reactor. In implementing the reaction, it is to be ensured that the chlorinating agent entrained by the reaction exit gases is replaced by introducing additional chlorinating agent.

It may expressly be pointed out that, in a further variant of the process according to the invention, further hydrogen chloride can be added even after discharge from the reaction apparatus. This can be carried out, for example, in a further apparatus, for example a stirred-tank reactor, situated between the reaction apparatus and the separating vessel. In addition, it is also possible to only introduce the hydrogen chloride subsequently. In this case, the reaction with the chlorinating agent takes place without the introduction of hydrogen chloride.

Preferably, the carbonyl chlorides are prepared by the process according to the invention by reacting the corresponding carboxylic acids with phosgene as chlorinating agent.

Carbonyl chlorides which can be prepared by the process according to the invention are, for example, those of the formula (II)

(II)

in which R stands for the following radicals:
$C_1$- to $C_{30}$-alkyl or their aryl- or cycloalkyl-substituted components:
saturated, straight-chain or branched hydrocarbon radical having from 1 to 30 carbon atoms, preferably methyl, ethyl, propyl, 1-methylethyl, butyl, 1-methylpropyl, 2-methylpropyl, 1,1-dimethylethyl, pentyl, 1-ethylpropyl, hexyl, heptyl, 1-ethylpentyl, octyl, 2,4,4-trimethylpentyl, nonyl, 1,1-dimethylheptyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl, diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl;

$C_3$- to $C_{12}$-cycloalkyl or their aryl- or cycloalkyl-substituted components:
monocyclic, saturated hydrocarbon radical having from 3 to 12 ring carbon atoms, preferably cyclopentyl, cyclohexyl;

$C_2$- to $C_{30}$-alkenyl or their aryl- or cycloalkyl-substituted components:
unsaturated, straight-chain or branched hydrocarbon radical having from 1 to 30 carbon atoms and 1 to 5 double bonds at any position, preferably 2-propenyl, 3-butenyl, cis-2-butenyl, trans-2-butenyl, cis-8-heptadecenyl, trans-8-heptadecenyl, cis,cis-8,11-heptadecadienyl, cis,cis,cis-8,11,14-heptadecatrienyl;

$C_3$- to $C_{12}$-cycloalkenyl or their aryl- or cycloalkyl-substituted components:
monocyclic, unsaturated hydrocarbon radical having from 3 to 12 ring carbon atoms and 1 to 3 double bonds at any position, preferably 3-cyclopentenyl, 2-cyclohexenyl, 3-cyclohexenyl, 2,5-cyclohexadienyl;

$C_2$- to $C_{30}$-alkynyl or their aryl- or cycloalkyl-substituted components:
unsaturated, straight-chain or branched hydrocarbon radical having from 1 to 30 carbon atoms and 1 to 3 triple bonds at any position, preferably 3-butynyl, 4-pentynyl;

$C_4$- to $C_{30}$-alkenynyl or their aryl- or cycloalkyl-substituted components:
unsaturated, straight-chain or branched hydrocarbon radical having from 1 to 30 carbon atoms, 1 to 3 triple bonds and 1 to 3 double bonds at any position.

Using the process according to the invention, it is also possible to prepare mixtures of said carbonyl chlorides. Non-limiting examples which may be mentioned are mixtures comprising $C_8$- to $C_{18}$-carbonyl chlorides, which are traded under the trivial names "carboxylic acid chloride", "tallow fatty acid chloride", "coconut fatty acid chloride" and "oleic acid chloride".

Particular preference is given to preparing carbonyl chlorides of the formula (III) by the process according to the invention, in which R stands for the following radicals:

$C_1$- to $C_{30}$-alkyl or their aryl- or cycloalkyl-substituted components:
saturated, straight-chain or branched hydrocarbon radical having from 1 to 30 carbon atoms, preferably methyl, ethyl, propyl, 1-methylethyl, butyl, 1-methylpropyl, 2-methylpropyl, 1,1-dimethylethyl, pentyl, 1-ethylpropyl, hexyl, heptyl, 1-ethylpentyl, octyl, 2,4,4-trimethylpentyl, nonyl, 1,1-dimethylheptyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosy, octacosyl, nonacosyl, triacontyl, phenylmethyl, diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl;

$C_2$- to $C_{30}$-alkenyl or their aryl- or cycloalkyl-substituted components:
unsaturated, straight-chain or branched hydrocarbon radical having from 1 to 30 carbon atoms and 1 to 5 double bonds at any position, preferably 2-propenyl, 3-butenyl, cis-2-butenyl, trans-2-butenyl, cis-8-heptadecenyl, trans-8-heptadecenyl, cis,cis-8,11-heptadecadienyl, cis,cis,cis-8, 11, 14-heptadecatrienyl;

and mixtures thereof.

Very particularly preferably, the process according to the invention is used to prepare acetyl chloride (R=methyl), propionyl chloride (R=ethyl), butyryl chloride (R=propyl), valeryl chloride (R=butyl), isovaleryl chloride (R=2-methylpropyl), pivaloyl chloride (R=1,1-dimethylethyl), caproyl chloride (R=pentyl), 2-ethylbutyryl chloride (R=1-ethylpropyl), enanthyl chloride (R=hexyl), capryloyl chloride (R=heptyl, 2-ethylhexanoyl chloride (R=1-ethylpentyl), pelargonoyl chloride (R=octyl), isononanoyl chloride (R=2,4,4-trimethylpentyl), capryl chloride (R=nonyl), neodecanoyl chloride (R=1,1-dimethylheptyl), lauroyl chloride (R=undecyl), myristoyl chloride (R=tridecyl), palmitoyl chloride (R=pentadecyl), stearoyl chloride (R=heptadecyl), oleoyl chloride (R=cis-8-heptadecenyl), linoleoyl chloride (R=cis, cis-8,11-heptadecadienyl), linolenoyl chloride (R=cis,cis,cis-8,11,14-heptadecatrienyl), arachidoyl chloride (R=nonadecyl) and behenoyl chloride (R=henicosyl) and mixtures thereof.

The carboxylic acids to be used for the process according to the invention arise from the above-described definitions for R. It may be pointed out that mixtures of the various carboxylic acids can also be chlorinated using the process according to the invention.

In a general variant for the batchwise preparation of the carbonyl chlorides by chlorination by means of thionyl chloride, the total amount of the corresponding carboxylic acid is initially introduced into a stirred tank reactor, and the required amount of N,N-disubstituted formamide (I) is metered in with stirring. The reaction system is then brought to the desired temperature, and liquid thionyl chloride is continuously metered in at atmospheric pressure with further vigorous stirring. The gaseous products sulfur dioxide and hydrogen chloride formed are drawn off. With regard to the amount of thionyl chloride introduced, it is to be ensured that only a low concentration of catalyst adduct is still present following the reaction. When the thionyl chloride addition is complete, N,N-disubstituted formamide is again added with further stirring. Gaseous hydrogen chloride is then introduced where, in the determination of the amount introduced, the total amount of N,N-disubstituted formamide added, i.e. before and after chlorination, is decisive. For the addition rate of the hydrogen chloride introduction, a good uptake in the reaction solution is to be ensured. If necessary, the rate of addition must be lowered. Also after the hydrogen chloride addition is complete, the reaction solution can be further stirred. The mixing is then stopped so that the two phases can separate. The lower, catalyst-containing phase is separated off and can be reused in further syntheses. The carbonyl chloride phase which is left is freed from residual hydrogen chloride and sulfur dioxide by passing nitrogen through it, and can then be used for further synthesis stages, usually without additional purification steps.

In a general variant for the batchwise preparation of the carbonyl chlorides by chlorination by means of phosgene, the total amount of the corresponding carboxylic acid is introduced into a stirred tank reactor, and the required amount of N,N-disubstituted formamide (I) is metered in with stirring. The reaction system is then brought to the desired temperature and, at atmospheric pressure and with further vigorous stirring, gaseous or liquid phosgene and gaseous hydrogen chloride are continuously introduced until the equimolar amount with regard to the carboxylic acid used and additionally a slight excess of phosgene have been introduced into the reaction mixture. The gaseous products carbon dioxide and hydrogen chloride formed are drawn off. With regard to the amount of phosgene added, it must be ensured that only a low concentration of catalyst adduct is still present following the reaction. Depending on the variant, it is possible to stop the introduction of the hydrogen chloride with the end of the phosgene addition, or else to continue beyond the end of the phosgene addition. The total amount of hydrogen chloride introduced should, however, based on the amount of N,N-disubstituted formamide (I), advantageously be within the range given. After the addition of the hydrogen chloride is complete, the reaction solution is stirred for a further 1 to 2 hours. The mixing is then stopped so that the two phases can separate. The lower, catalyst-containing phase is separated off and can be reused in further syntheses. The carbonyl chloride phase which is left is freed from residual hydrogen chloride and carbon dioxide by passing nitrogen through it, and can then be used for further synthesis stages, usually without additional purification steps.

In a general variant for the continuous preparation of the carbonyl chlorides by chlorination by means of phosgene, the carboxylic acid, recycled catalyst adduct, optionally fresh N,N-disubstituted formamide (I), gaseous or liquid phosgene and gaseous hydrogen chloride are continuously introduced into a stirred tank reactor with vigorous stirring at the desired temperature under atmospheric pressure. The rate of addition of the phosgene is dependent on that of the carboxylic acid, and the rate of addition of the hydrogen chloride is dependent on that of the catalyst adduct or of the N,N-disubstituted formamide (I). Particularly in the case of the introduction of.the phosgene, it must be ensured that only a low concentration of catalyst adduct is still present in the drawn-off solution. An amount corresponding to the introduced amount is continuously drawn off from the stirred tank reactor and passed to a separating vessel. From this, the catalyst-containing phase, which is generally the lower phase, is continuously drawn off and returned to the stirred tank reactor. The carbonyl chloride phase which is left is removed from the separating vessel and, in a further vessel, freed from residual hydrogen chloride and carbon dioxide by passing nitrogen through it. It can then be used for further synthesis stages, usually without additional purification steps.

A further general variant for the continuous preparation of the carbonyl chlorides by chlorination by means of phosgene differs from that just described in that the phosgenation is carried out in a stirred tank reactor or a battery of stirred tank reactors consisting of 2 to 3 stirred tank reactors, without the introduction of hydrogen chloride. The reaction solution which is continuously drawn off is passed to a further stirred tank reactor situated between the stirred tank reactor or the battery of stirred tank reactors and the separating vessel. Here, the continuous treatment with the hydrogen chloride takes place. The extracted reaction solution is then passed to the separating vessel and further treated as described above.

An essential feature of the preparation of the carbonyl chlorides having a low color number according to the invention and as described above is the surprising effect that precisely the color-imparting components are considerably more soluble in the hydrogen-chloride-containing phase of the N,N-disubstituted formamide (I) than in the carbonyl-chloride-containing phase.

The process according to the invention leads, mainly by virtue of the measure of introducing hydrogen chloride, which can be readily integrated into the synthesis process, to carbonyl chlorides with a low color number, meaning that they can be usually used for subsequent reactions without distillation, separate extraction or adsorptive treatment. The process according to the invention can be carried out very effectively and economically. By avoiding the distillation which is customary according to the prior art, both investment and energy costs are saved, and also as a rule a higher yield of purified carbonyl chloride is achieved. For distillation-sensitive carbonyl chlorides, the process according to the invention opens up the possibility of an economical synthesis on an industrial scale.

EXAMPLES

Comparative Example 1

Preparation of Lauroyl Chloride 82.2 g (1.13 mol) of N,N-dimethylformamide were added to 4.5 mol of lauric acid in a stirred apparatus. The reaction solution was brought to a temperature of from 40 to 50° C. with stirring, and a total of 5.06 mol of gaseous phosgene were introduced under atmospheric pressure. After the addition of phosgene was complete, the two phases were separated from one another. The catalyst phase comprised a molar proportion of the catalyst adduct, based on the molar amount of N,N-dimethylformamide plus catalyst adduct, of 0.50. The carbonyl chloride phase comprised 99.1 area % of lauroyl chloride and 0.15 area % of lauric acid. The color number was 268 APHA.

As a result of a relatively high molar ratio between the phosgene introduced and the lauric acid used, a high conversion to lauroyl chloride was achieved. The carbonyl-chloride-containing phase, however, has an unsatisfactory, high color number.

Comparative Example 2

Preparation of Pelargonoyl Chloride (Nonanoyl Chloride)

100.5 g (1.38 mol) of N,N,-dimethylformamide were added to 2.75 mol of pelargonic acid in a stirred apparatus. The reaction solution was brought to a temperature of from 20 to 30° C. with stirring, and a total of 2.78 mol of gaseous phosgene were introduced under atmospheric pressure. After the addition of phosgene was complete, the two phases were separated from one another. The catalyst phase comprised a molar proportion of the catalyst adduct, based on the molar amount of N,N-dimethylformamide plus catalyst adduct, of <0.05. The carbonyl chloride phase comprised 97.1 area % of pelargonoyl. chloride and 1.9 area % of pelargonic anhydride. The color number was 16 APHA.

As a result of a very low, virtually stoichiometric molar ratio between the phosgene introduced and the pelargonic acid used, only an unsatisfactorily low content of pelargonoyl chloride was achieved in the crude product, with too high a content of pelargonic anhydride. However, the carbonyl-chloride-containing phase exhibits a very low color number.

Example 3
Preparation of Pelargonoyl Chloride (Nonanoyl Chloride)

100.5 g (1.38 mol) of N,N-dimethylformamide were added to 2.75 mol of pelargonic acid in a stirred apparatus. The reaction solution was brought to a temperature of from 20 to 30° C. with stirring, and a total of 2.78 mol of gaseous phosgene and simultaneously 1.92 mol of gaseous hydrogen chloride were introduced under atmospheric pressure. When the addition of phosgene and hydrogen chloride was complete, the two phases were separated from one another. The catalyst phase comprised a molar proportion of the catalyst adduct, based on the molar amount of N,N-dimethylformamide plus catalyst adduct, of 1%. The carbonyl chloride phase comprised 98.9% by weight of pelargonoyl chloride and 0.04% by weight of pelargonic anhydride. The color number was 18 APHA.

Only as a result of the simultaneous introduction of hydrogen chloride according to the invention was it possible to obtain a high conversion to pelargonoyl chloride having a very low color number.

Comparative Example 4
Preparation of Coconut Fatty Acid Chloride 36.6 g (0.5 mol) of N,N-dimethylformamide were added to 2.0 mol of coconut fatty acid (trade name HK 8-18, Henkel), which consists essentially of lauric acid and myristic acid, in a stirred apparatus. The reaction solution was brought to a temperature of 30° C. with stirring, and a total of 2.38 mol of gaseous phosgene were introduced under atmospheric pressure. After the addition of phosgene was complete, the two phases were separated from one another. The catalyst phase comprised a molar proportion of the catalyst adduct, based on the molar amount of N,N-dimethylformamide plus catalyst adduct, of 0.50. The carbonyl chloride phase comprised 99.6% by weight of coconut fatty acid chloride and 0.35% by weight of coconut fatty acid. The color number was 399 APHA.

As a result of a relatively high molar ratio between the phosgene introduced and the coconut fatty acid used, a high conversion to coconut fatty acid chloride was achieved. However, the carbonyl-chloride-containing phase exhibits an unsatisfactory, high color number.

Example 5
Preparation of Coconut Fatty Acid Chloride 73.1 g (1.0 mol) of N,N-dimethylformamide were added to 2.01 mol of coconut fatty acid (trade name HK 8-18, Henkel) in a stirred apparatus. The reaction solution was brought to a temperature of 30° C. with stirring, and a total of 2.1 mol of gaseous phosgene and simultaneously 1.04mol of gaseous hydrogen chloride were introduced under atmospheric pressure. When the addition of phosgene and hydrogen chloride were complete, the two phases were separated from one another. The catalyst phase comprised a molar proportion of the catalyst adduct, based on the molar amount of N,N-dimethylformamide plus catalyst adduct, of <0.10. The carbonyl chloride phase comprised 99.5% by weight of coconut fatty acid chloride and 0.5% by weight of coconut fatty acid. The color number was 44 APHA.

Only as a result of the simultaneous introduction of hydrogen chloride according to the invention was it possible to obtain a high conversion to coconut fatty acid chloride with a very low color number.

The examples show that, irrespective of the type of carboxylic acid, by simultaneously introducing hydrogen chloride gas in the reaction with the chlorinating agent, a high conversion to the desired carbonyl chloride with very low color numbers is achieved. The carbonyl chlorides obtained in the examples according to the invention can be used in subsequent syntheses without further purification steps.

We claim:

1. A process for the preparation of carbonyl chlorides by reacting carboxylic acids with phosgene or thionyl chloride in the presence of a catalyst adduct of an N,N-disubstituted formamide of the formula (I) in which $R^1$ and $R^2$ independently of one another are $C_1$- to $C_4$-alkyl or $R^1$ and $R^2$

(I)

together are a $C_4$- or $C_5$-alkylene chain and phosgene or thionyl chloride, which comprises introducing gaseous hydrogen chloride during the reaction.

2. A process as claimed in claim 1, wherein, overall, a molar amount of gaseous hydrogen chloride of 0.2 to 2.0, based on the molar amount of carboxylic acid employed, is used.

3. A process as claimed in claim 1, wherein, in the reaction with phosgene, a molar amount of N,N-disubstituted formamide (I) of 0.05 to 2.0, based on the molar amount of carboxylic acid employed, is used.

4. A process as claimed in claim 1, wherein, in the reaction with thionyl chloride, a molar amount of N,N-disubstituted formamide (I) of 0.001 to 0.05, based on the molar amount of carboxylic acid employed, is used.

5. A process as claimed in claim 1, wherein, during the reaction, a molar amount of phosgene or thionyl chloride of 1.0 to 2.0, based on the molar amount of carboxylic acid, is used.

6. A process as claimed in claim 1, wherein the molar proportion of the catalyst adduct of the N,N-disubstituted formamide (I) and phosgene or thionyl chloride, based on the molar amount of N,N-disubstituted formamide (I) plus catalyst adduct, is less than 0.3 after the reaction.

7. A process as claimed in claim 1, wherein the molar proportion of the catalyst adduct of the N,N-disubstituted formamide (I) and phosgene or thionyl chloride, based on the molar amount of N,N-disubstituted formamide (I) plus catalyst adduct, is less than 0.1 after the reaction.

8. A process as claimed in claim 1, wherein the carbonyl chloride is isolated from the reaction mixture following the reaction by phase separation.

9. A process as claimed in claim 1, wherein the N,N-disubstituted formamide (I) used is N,N-dimethylformamide.

10. A process as claimed in claim 1, wherein, following the reaction, the N,N-disubstituted formamide (I), its hydrochloride and catalyst adduct are separated off and reused as catalyst precursor in the carbonyl chloride synthesis.

11. A process as claimed in claim 1, wherein the carboxylic acids are reacted with phosgene.

12. A process as claimed in claim 1, wherein the carbonyl chlorides prepared are acetyl chloride, propionyl chloride, butyryl chloride, valeryl chloride, isovaleryl chloride, pivaloyl chloride, caproyl chloride, 2-ethylbutyryl chloride, enanthyl chloride, capryloyl chloride, 2-ethylhexanoyl chloride, pelargonoly chloride, isononanoyl chloride, capryl chloride, neodecanoyl chloride, lauroyl chloride, myristoyl chloride, palmitoyl chloride, stearoyl chloride, oleoyl chloride, linoleoyl chloride, linolenoyl chloride, arachidoyl chloride and behenoyl chloride, and mixtures thereof.

* * * * *